United States Patent
Edvinsson et al.

(10) Patent No.: US 10,995,077 B2
(45) Date of Patent: May 4, 2021

(54) PROCESS TO PREPARE HIGHER ETHYLENE AMINES AND ETHYLENE AMINE DERIVATIVES

(71) Applicant: Akzo Nobel Chemicals International B.V., Arnhem (NL)

(72) Inventors: Rolf Krister Edvinsson, Partille (SE); Eike Nicolas Kantzer, Uddevalla (SE); Per Fredrik Olmo Larsson, Gothenburg (SE); Karl Fredrik Lake, Södertälje (SE); Antoon Jacob Berend Ten Kate, Arnhem (NL); Ina Ehlers, Stenungsund (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/076,463

(22) PCT Filed: Feb. 10, 2017

(86) PCT No.: PCT/EP2017/052945
§ 371 (c)(1),
(2) Date: Aug. 8, 2018

(87) PCT Pub. No.: WO2017/137530
PCT Pub. Date: Aug. 17, 2017

(65) Prior Publication Data
US 2019/0047971 A1    Feb. 14, 2019

(30) Foreign Application Priority Data

Feb. 12, 2016  (EP) ................................. 16155545
Feb. 12, 2016  (EP) ................................. 16155549

(51) Int. Cl.
C07D 295/13  (2006.01)
C07D 233/36  (2006.01)
C07D 295/023  (2006.01)

(52) U.S. Cl.
CPC ......... *C07D 295/13* (2013.01); *C07D 233/36* (2013.01); *C07D 295/023* (2013.01)

(58) Field of Classification Search
None
See application file for complete search history.

(56) References Cited

U.S. PATENT DOCUMENTS

| | | |
|---|---|---|
| 2,812,333 A | 11/1957 | Steele |
| 4,111,840 A | 9/1978 | Best |
| 4,387,249 A | 6/1983 | Harnden et al. |
| 4,503,250 A | 3/1985 | Herdle |
| 4,568,745 A | 2/1986 | Ghelli et al. |
| 4,650,906 A | 3/1987 | Murakami et al. |
| 4,683,337 A | 7/1987 | Budde |
| 4,684,729 A | 8/1987 | Duquette et al. |
| 4,758,354 A | 7/1988 | O'Mara et al. |
| 4,897,480 A | 1/1990 | Schoenleben |
| 5,112,984 A | 5/1992 | Richey, Jr. et al. |
| 5,262,534 A | 11/1993 | King |
| 5,364,971 A | 11/1994 | Su |
| 5,491,263 A | 2/1996 | Rooney et al. |
| 5,861,537 A | 1/1999 | Shinohara et al. |
| 8,188,318 B2 | 5/2012 | Petraitis et al. |

(Continued)

FOREIGN PATENT DOCUMENTS

| | | |
|---|---|---|
| CH | 478 180 A | 9/1969 |
| DE | 1 510 538 | 5/1978 |

(Continued)

OTHER PUBLICATIONS

Davis ("Thermal Degradation of Aqueous Amines Used for Carbon Dioxide Capture" Ph.D. dissertation, 2009, The University of Texas at Austin, retrieved from http://rochelle.che.utexas.edu/files/2015/02/Davis-2009- Thermal-Degradation-of-Aqueous-Amines-Used-for-Carbon-Dioxide-Capture.pdf on Feb. 10, 2019) (Year: 2009).*
P.K. Shenoy et al., "2-Imidazolidinones (Ethylene Ureas)—A Review"; American Dyestuff Reporter; May 1968; p. 17-34.
Namjoshi, et al.; "In Situ Synthesis of Useful Polyamines for $CO_2$ Capture From Piperazine"; AIChE Annual Meeting Conference 2012; 10 pages.
Lepaumier et al., "Study on the Degradation Mechanisms of New Amines in the Presence of $CO_2$ or $O_2$"; LMOPS; Jun. 15, 2009-Trondheim; 42 pgs.
Lepaumier et al., "New Amines for $CO_2$ Capture. I. Mechanisms of Amine Degradation in the Presence of $CO_2$"; Industrial & Engineering Chemistry Research 2009, vol. 48, pp. 9061-9067.

(Continued)

*Primary Examiner* — Amy C Bonaparte
(74) *Attorney, Agent, or Firm* — Lorenz & Kopf, LLP

(57) ABSTRACT

The present invention relates to a process to prepare ethyleneamines of the formula $NH_2$—$(C_2H_4$—NH—$)_p$H wherein p is at least 2 wherein one or more units —NH—$C_2H_4$—NH— are present as a piperazine unit or precursors thereof wherein optionally one or more units —NH—$C_2H_4$—NH— are present as a cyclic ethylene urea unit or between two units —NH—$C_2H_4$—NH— a carbonyl moiety is present, by reacting an ethanolamine-functional compound, an amine-functional compound in the presence of a carbon oxide delivering agent, wherein at least one of the amine-functional compound or the ethanolamine-functional compound contains a piperazine unit, and the reaction is performed in a liquid that comprises water.

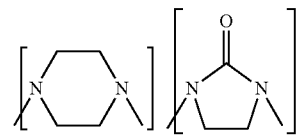

15 Claims, No Drawings

(56) References Cited

U.S. PATENT DOCUMENTS

| | | |
|---|---|---|
| 8,383,860 B2 | 2/2013 | Cook et al. |
| 8,440,852 B2 | 5/2013 | Dahmen et al. |
| 8,513,435 B2 | 8/2013 | Baloche et al. |
| 9,321,007 B2 | 4/2016 | Rochelle et al. |
| 10,428,011 B2 | 10/2019 | Edvinsson et al. |
| 2010/0094007 A1 | 4/2010 | King et al. |
| 2010/0120983 A1 | 5/2010 | Dufaure et al. |
| 2010/0121064 A1 | 5/2010 | Dahmen et al. |

FOREIGN PATENT DOCUMENTS

| | | |
|---|---|---|
| EP | 0 075 935 A2 | 4/1983 |
| EP | 0 222 934 A1 | 5/1987 |
| EP | 1 654 214 B1 | 3/2007 |
| FR | 2912148 A1 | 8/2008 |
| JP | S5285991 A | 7/1977 |
| JP | S56108534 A | 8/1981 |
| JP | S60-120842 A | 6/1985 |
| JP | S60-126248 A | 7/1985 |
| JP | H01500357 A | 2/1989 |
| JP | 2012504611 A | 2/2012 |
| WO | 2011/079008 A1 | 6/2011 |
| WO | 2013/110092 A1 | 7/2013 |
| WO | 2017/137531 A1 | 8/2017 |
| WO | 2017/137532 A1 | 8/2017 |
| WO | 2017137529 A1 | 8/2017 |

OTHER PUBLICATIONS

Lepaumier et al.; "New Amines for $CO_2$ Capture. II. Oxidative Degradation Mechanisms"; Industrial & Engineering Chemistry Research 2009, vol. 48, pp. 9068-9075.

Lepaumier et al.; "New Amines for $CO_2$ Capture. III. Effect of Alkyl Chain Length Between Amine Functions on Polyamines Degradation" Industrial & Engineering Chemistry Research 2010, vol. 49, pp. 4553-4560.

Huntsman Corporation Brochure; "Ethyleneamines: A Global Profile of Products and Services"; 2007; 76 pgs.

Brissault et al.; "Synthesis of Linear Polyethylenimine Derivatives for DNA Transfection" Bioconjugate Chemistry; vol. 14, No. 3, 2003; pp. 581-587.

Stapleton; "A Simple Method of Polyamine Purification"; Australian Journal of Chemistry 1985, vol. 38, pp. 633-666.

Global CCS Institute; "3.2 Thermal Degradation of MEA"; 4 pgs. downloaded Sep. 11, 2018.

CSIRO—Australian National Low Emissions Coal Research and Development; Project: Environmental Impacts of Amine-based $CO_2$ Post Combustion Capture (PCC) Process; 2012; 116 pgs.

International Search Report and Written Opinion for PCT/EP2017/052945 dated Apr. 21, 2017.

The Dow Chemical Company Brochure; "Ethyleneamines"; Aug. 2001 ; 48 pgs.

* cited by examiner

PROCESS TO PREPARE HIGHER ETHYLENE AMINES AND ETHYLENE AMINE DERIVATIVES

This application is a national stage filing under 35 U.S.C. § 371 of PCT/EP2017/052945, filed Feb. 10, 2017, which claims priority to European Patent Application No. 16155545.3, filed Feb. 12, 2016 and European Patent Application No. 16155549.5, filed Feb. 12, 2016, the contents of which are each incorporated herein by reference in their entireties.

The present invention relates to a process for making piperazine unit-containing higher ethylene amines (EA), i.e. ethylene amines and derivatives (or precursors) thereof, like urea derivatives, that contain ethylene units and amine groups and at least one piperazine unit

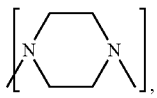

wherein "higher" denotes that the amine contains at least 3 ethylene units, by reacting an ethanolamine functional compound with an amine functional compound in the presence of a carbon oxide delivering agent wherein at least one of the reactants contains a piperazine unit.

Ethylene amines consist of two or more nitrogen atoms linked by ethylene units. Ethylene amines can be present in the form of linear chains $H_2N(-C_2H_4NH)_p-H$. For p=1, 2, 3, 4, . . . these are denoted EDA, DETA, L-TETA, L-TEPA, . . . .

With three or more ethylene units it is also possible to create branched ethylene amines such as $N(CH_2CH_2NH_2)_3$, TAEA. Two adjacent nitrogen atoms linked by two ethylene units are called a piperazine ring

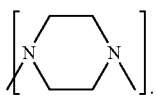

Piperazine rings can be present in longer chains to produce the corresponding cyclic ethylene amines.

Two adjacent nitrogen atoms linked by one ethylene unit and one carbonyl moiety form a cyclic ethylene urea (EU). An ethylene amine (EA) in which two nitrogen atoms are linked intramolecular by a carbonyl moiety

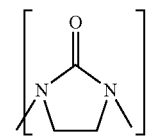

is here referred to as an UEA. Replacing the carbonyl moiety with two hydrogen atoms yields the corresponding ethylene amine. For example: EU↔EDA, UDETA↔DETA, UAEEA↔AEEA, UTETA↔L-TETA, UTEPA↔L-TEPA. Some higher amines can host more than one carbonyl moiety, e.g. DUTETA, the diurea of L-TETA. The carbonyl moiety may link nitrogen atoms on two separate molecules, which gives a linear urea. For example $H_2NC_2H_4NH-CO-NHC_2H_4NH_2$ and replacing the carbonyl moiety with two hydrogen atoms here yields two EDA.

Each amine function in ethylene amines and ethylene ureas can be primary, secondary or tertiary. Furthermore, a secondary amine can be linear (linear secondary amines, LSA) or cyclic (cyclic secondary amine, CSA).

In the presence of any Brønsted acid (such as water) ethylene amines (EA) can be protonated (EAH$^+$). If not otherwise stated the term amine in this document will include both the protonated and unprotonated form.

Some ethylene amines and urea derivatives thereof are shown below as an illustration. This can naturally be extended to include a.o. pentamines, hexamines and so on.

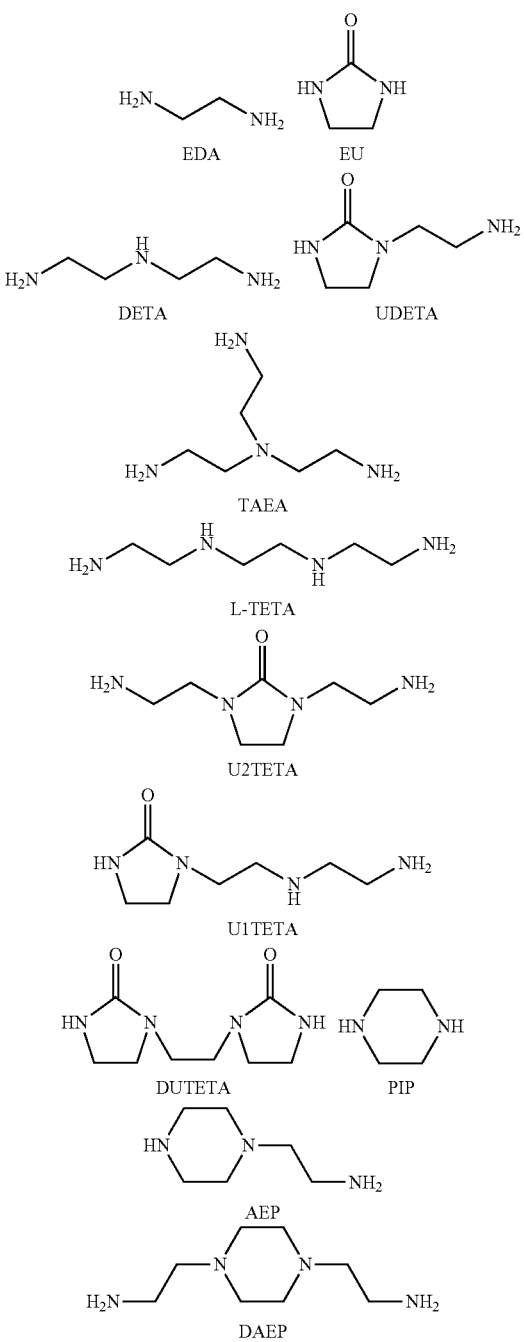

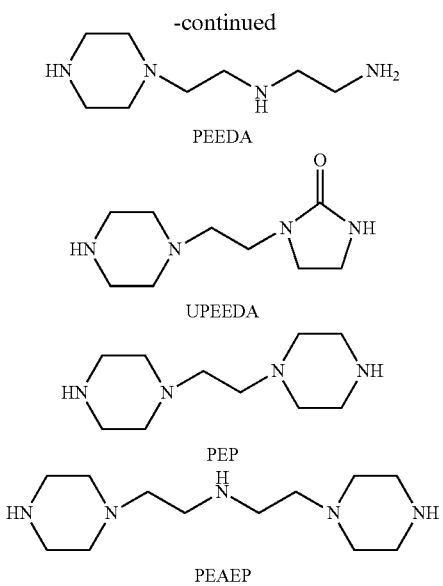

As to naming of the molecules, EDA stands for ethylenediamine, DETA for diethylenetriamine, TETA for triethylenetetraamine, TEPA for tetraethylenepentamine, PEHA for pentaethylenehexamine. When there is a single cyclic urea in the molecule this is indicated by adding a U in front of the name, i.e. UTETA means the cyclic urea of TETA, while when there are two cyclic ureas in the molecule this is indicated by DU, i.e. DUTETA means the internal cyclic diurea of TETA. If there is a number indicated for the U this refers to the amino group where the U group is located. There is one exception to this naming and that is that instead of UEDA the abbreviation EU is used, which stand for ethyleneurea, Furthermore, TAEA stands for trisaminoethylamine, PIP stands for piperazine, AEP for aminoethyl piperazine, DAEP stands for diaminoethyl piperazine, PEP stands for piperazinoethyl piperazine, PEEDA for piperazinoethyl ethylenediamine, PEAEP for piperazinoethyl aminoethylpiperazine The manufacturing of ethylene amines is presently dominated by two routes. These are the reductive amination of MEA and the EDC route.

Reductive amination of MEA proceeds in the presence of a hydrogenation/dehydrogenation catalyst in an excess of ammonia. Next to the reductive amination of MEA to give EDA a number of side reactions including transamination produce a mixture of a large number of ethylene and ethanolamines. The output is dominated by mono and diethylene products (EDA, DETA, PIP and AEEA). Higher ethylene and ethanolamines are also formed but the mixture is complex and ineffective in producing high yields of specific molecules with high selectivity.

Nowadays there is a high demand for higher ethylene amines and hence there is a need for a process for selectively making specific ethylene amines with an improved yield. Especially, there is a need for a process to substitute cyclic secondary amine with chains that contain a primary amine with good yield and selectivity. Furthermore there is a need for such a process for making substituted piperazines that does not co-generate large amounts of waste salt.

U.S. Pat. No. 5,262,534 discloses a process to react piperazine with oxazolidinone which is a carbamate of monoethanolamine and hence discloses a reaction of piperazine with an alkanolamine and carbonyl delivering agent in one compound. In the best example yields of 27.48 area-% of mono and 5.81 area-% of diaminoethylpiperazine is obtained. The reactions are performed in a solvent-free setup The present invention now provides a process to prepare ethyleneamines of the formula $NH_2$—$(C_2H_4$—$NH$—$)_pH$ wherein p is at least 2 wherein one or more units —NH—$C_2H_4$—NH— are present as a piperazine unit or derivatives thereof, wherein optionally one or more units —NH—$C_2H_4$—NH— are present as a cyclic ethylene urea unit or between two units —NH—$C_2H_4$—NH— a carbonyl moiety is present, by reacting an ethanolamine-functional compound with an amine-functional compound in the presence of a carbon oxide delivering agent, wherein the reaction is performed in a liquid wherein the liquid comprises water.

It was found that when performing the reaction in the mentioned liquid both the yield and selectivity can be increased. Even if one or more of the ethanolamine-functional compound, amine-functional compound or carbon oxide delivering agent are liquid at the reaction conditions, these are not considered part of the above liquid in which the process of the invention is performed.

In a preferred embodiment the liquid contains at least 50 wt-% of water up to 100 wt-% of water, wherein more preferably the remaining up to 50 wt-% is a polar liquid that mixes homogenously with water at the conditions employed during the process of the invention. Even more preferably the liquid contains at least 75 wt-% of water, yet more preferably at least 90 wt-%, most preferably at least 95-wt % on total liquid weight.

In another preferred embodiment the molar ratio between water and the amine-functional compound is greater than 0.2, preferably greater than 0.5 and most preferably greater than 1. In a preferred embodiment the ratio is lower than 200.

The amine-functional compound is a compound containing one or more amine groups, preferably at least two amine groups, and no alcohol groups.

The ethanolamine-functional compound is a compound containing one hydroxyl group linked via an ethylene to an amine group that optionally may be present as its carbamate equivalent or cyclic carbamate equivalent.

At least one of the amine-functional compound and the ethanolamine-functional compound contains one or more piperazine units

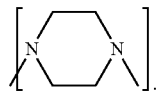

In a preferred embodiment in the process the ethanolamine-functional compound is of the formula HO—$(C_2H_4$—NH—$)_qH$ wherein q is at least 1 and the amine-functional compound is of the formula $NH_2$—$(C_2H_4$—NH—$)_rH$ wherein r is at least 1, wherein at least one q or r unit is present as a piperazine unit, and wherein optionally one or more q or r units may be present as a cyclic ethylene urea, cyclic ethylene carbamate or a further piperazine unit.

In a yet more preferred embodiment the piperazine unit is in the amine-functional compound.

More preferred the amine-functional compound contains at least one cyclic secondary amine group, and optionally more amine groups that may be primary, secondary and/or tertiary amines wherein the amine groups within the compound are linked to one another via ethylene groups, and optionally some by a carbonyl group, and/or an additional ethylene group (to give a piperazine or urea unit in the amine functional compound).

Even more preferred as amine-functional compounds are piperazine, piperazineethylenepiperazine (PEP), and the amine functional compounds shown below, wherein n is 0 or higher, m is 1 or higher, p is 1 or higher and o is 1 or higher.

| Cyclic EA isomers which cannot form UEA, not including branched ones |
| --- |

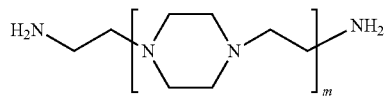

for even number of amine groups
e.g. TETA, PEHA etc.
m = 1: DAEP (AEPEA)
m = 2: AEPEPEA
m = 3: AEPEPEPEA
...

p = 1: AEPEAEP
p = 2: AEPEAEPEAEP
...

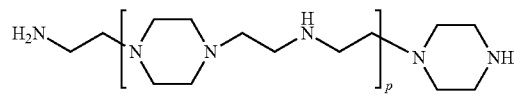

for uneven number of ethylene units
e.g. TEPA, HEHA etc.
n = 0: AEP
n = 1: PEPEA
n = 2: PEPEPEA
n = 3: PEPEPEPEA
...

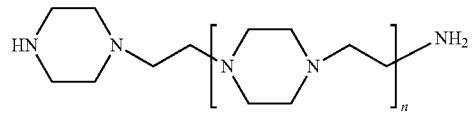

o = 1: PEAEP
o = 2: PEAEPEAEP
...

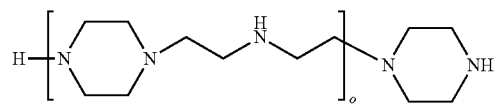

EXAMPLES

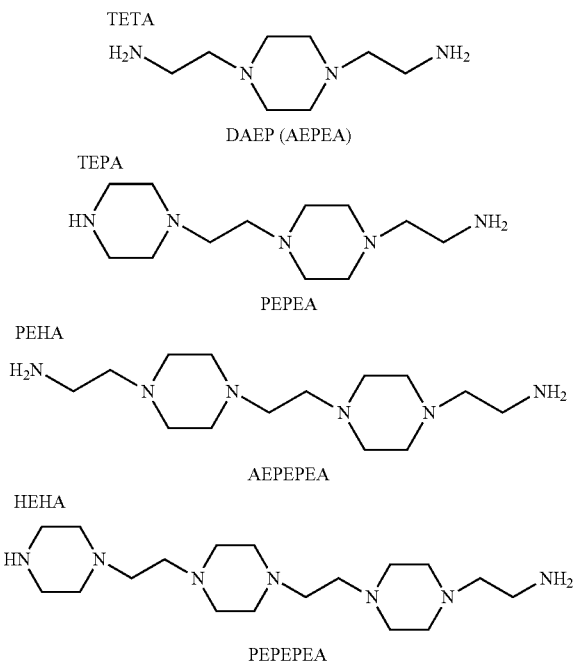

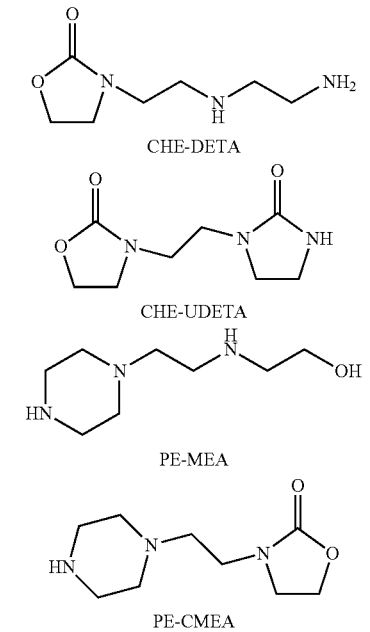

Most preferred the amine-functional compound comprises piperazine (PIP), aminoethylpiperazine (AEP), diaminoethylpiperazine (DAEP), piperazinoethyl ethylenediamine (PEEDA) or a linear urea thereof Generally, the ethanolamine-functional compound is of the following formula

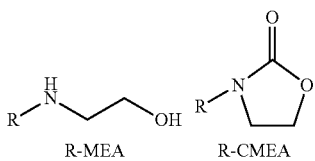

Where R in embodiments is a substituted or unsubstituted alkyl group which also can contain unsaturated moieties and heteroatoms, such as oxygen and nitrogen.

Examples of Ethanolamine Functional Compounds Include

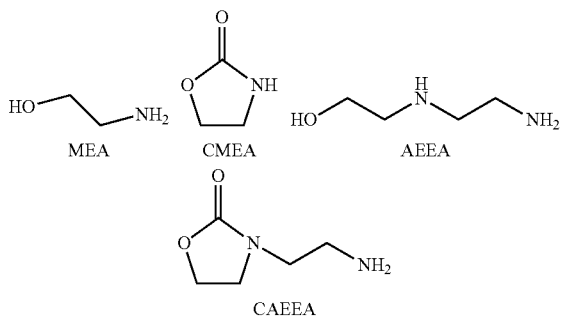

As to naming convention, MEA stands for monoethanolamine, AEEA stands for aminoethylethanolamine (also referred to as hydroxyethylethyleneamine), HE-DETA for hydroxyethyldiethylenetriamine, and from there on HE-TETA for hydroxyethyl triethylenetetramine etc. PE-MEA stands for piperazinoethylmonoethanolamine. By using the letter C it is indicated that a cyclic carbamate ring is present in the molecule.

The ethanolamine-functional compound is preferably monoethanolamine (MEA) or aminethylethanolamine (AEEA) or a cyclic or linear carbamate or urea thereof.

The carbon oxide delivering agent is a compound containing a carbonyl moiety that can be transferred to an ethanolamine functional compound leading to the formation of a cyclic carbamate, such as CMEA (2-oxazolidinone) or that can be transferred to an ethylene amine (EA) leading to the formation of the corresponding cyclic ethylene urea (UEA). Next to cyclic compounds linear carbamates and ureas may form as well.

Carbon oxide delivering agents within the scope of the present invention include carbon dioxide, and organic compounds in which a carbonyl moiety is available for being transferred as described above. Organic compounds in which a carbonyl moiety is available include urea and derivatives thereof; linear and cyclic alkylene ureas, especially cyclic urea, mono or di-substituted alkylene ureas, alkyl and dialkyl ureas, linear and cyclic carbamates, organic carbonates and derivatives or precursors thereof. Such derivatives or precursors may for example include ionic compounds such as carbonate or bicarbonate salts, carbamic acids and associated salts, that can be converted, in some embodiments in situ in the process of the invention, into their non-ionic counterparts, for example into linear and cyclic carbamate or urea compounds. When such ionic compounds are used in the present invention, they are organic hydrocarbon-based carbonate bicarbonate or carbamate salts. Preferably the CO delivering agent is CO2 or an organic compound that is suitable for use as a carbon oxide delivering agent and wherein alkylene is ethylene, or urea or ethylene carbonate, more preferably the carbon oxide delivering agent is at least partly added as carbon dioxide or urea. The carbon oxide delivering agent can be present in the process in the same molecule as the amine functional or the ethanolamine functional compound by using the aforementioned urea or carbamate compounds.

Examples of Carbon Oxide Delivering Agents Include

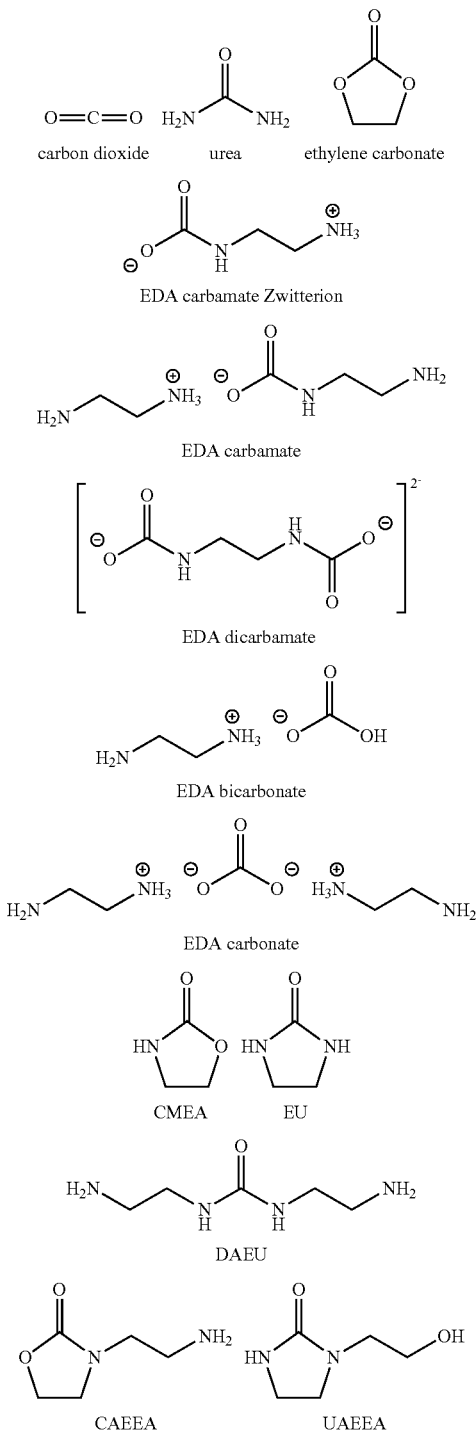

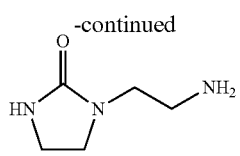

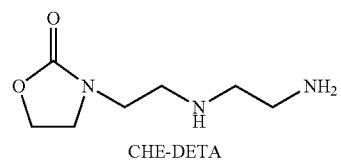

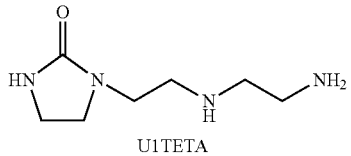

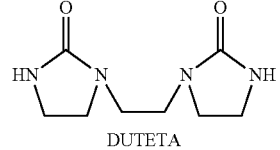

In the above drawing CAEEA again stands for the carbamate of aminoethylethanolamine, UDETA for the urea of diethylene triamine, DAEU stands for diaminoethyl urea, AE AE carbamate stands for amino ethyl aminoethanol carbamate, CHE-DETA stands for the carbamate of hydroxyethyldiethylene triamine, U1TETA stands for the terminal urea of triethylene tetramine, and DUTETA stands for the 1,3-diurea of triethylene tetramine.

The carbon oxide delivering agent is most preferably added to the reaction in the form of carbon dioxide, the carbamate derivative of the ethanolamine-functional compound or the urea derivative of the amine-functional compound, or a combination of these.

In a preferred embodiment using at least 0.7 molar equivalents of ethanolamine-functional compound to amine-functional compound and at least 0.05 molar equivalents of carbon oxide delivering agent on amine-functional compound, the selectivity of the reaction towards specific higher ethylene amines can be further increased.

In another preferred embodiment the molar ratio of carbon oxide delivering agent to amine functional compound is at least 0.2:1, even more preferably, the molar ratio of carbon oxide delivering agent to amine-functional compound is between 0.5:1 and 20:1

More preferably, the molar ratio of ethanolamine-functional compound to amine functional compound is between 0.8 and 5:1 and the molar ratio of carbon oxide delivering agent to amine functional compound is between 0.5:1 and 20:1, even more preferably, the molar ratio of ethanolamine-functional compound to amine-functional compound is between 0.7:1 and 2:1 and the molar ratio of carbon oxide delivering agent to amine-functional compound is between 0.7:1 and 3:1.

In yet another preferred embodiment piperazine can be reacted to give a disubstituted piperazine. It is to be understood that then the molar ratio of ethanolamine-functional compound to the amine-functional compound piperazine should be equal to, or even more preferred higher than, 2:1 as each equivalent of piperazine can be reacted with two equivalents of ethanolamine-functional compound.

It should be noted that compounds exist that contain more than one carbonyl moiety that can be released from the molecule for transfer to the ethanolamine-functional compound. When determining the molar ratio for such compounds there should be an adjustment for the molar amount of carbon oxide they can release for transfer to the ethanolamine-functional compound or otherwise contribute to the process of the invention.

Selecting the right molar amounts of the carbon oxide delivering agent on amine-functional compound was found to further improve selectivity and yield in the process of the invention.

The molar amount of carbon oxide delivering agent on amine-functional compound is determined by the reactants in the process, independent of the dosing regime used for the reactants.

The reaction mixture is characterized by containing as reactants ethanolamine-functional compound, amine-functional compound and carbon oxide delivering agent and can be roughly represented by below non-limiting scheme.

Scheme 1: Amine Functional Compound is a Cyclic Secondary Amine

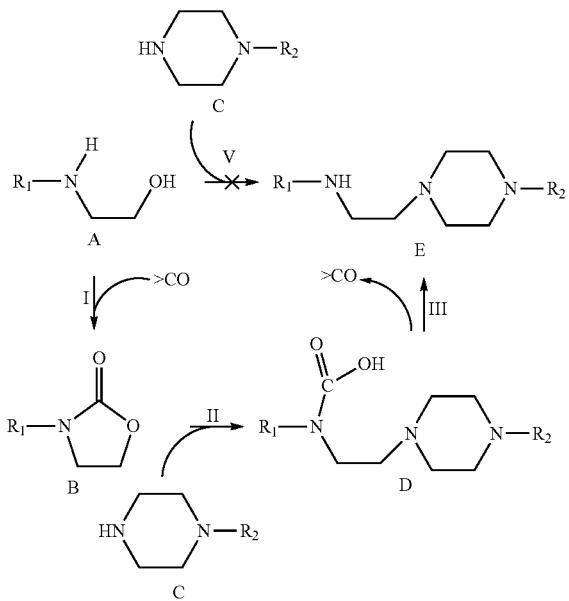

I Addition of CO to the ethanolamine to form the 2-oxazolidinone ring
II Chain extension by ring opening by cyclic secondary amine
III Removal of carbonyl group to form the ethylene amine
V Hypothetical direct uncatalyzed amination A number of reactions take place simultaneously when heating a mixture of a carbonyl source, an ethanolamine-functional compound and an amine-functional compound.

Without being bound to theory this can be summarized in two main reaction steps each composed of multiple sub steps: 1) the activation of the alcohol function (A) by the carbonyl group, the oxazolidinone (B) is assumed to be an intermediate, 2) the activated alcohol function is replaced by an amine (C) to give a chain extended primary addition product (D). In the presence of ammonia a conversion of the alcohol function to an amine function without giving a chain extension can take place as well. Optionally the CO groups can be removed leading to the formation of an ethylene amine (E).

Hence, in an embodiment of the process of the invention where the product composition that is obtained contains ethylene urea compounds, a next step is performed to convert obtained ethylene urea compounds into their corresponding ethylene amines, for example by hydrolyzing them.

Heating a suitable mixture of an ethanolamine, an amine that is not tertiary and a carbon oxide delivering agent to a relatively high temperature provides a way to produce a higher amine and CO containing derivative thereof that can serve as a carbon oxide delivering agent.

In another preferred embodiment the ethanolamine-functional compound and the carbon oxide delivering agent are at least partly added as one compound by using a carbamate adduct and/or the amine-functional compound and the carbon oxide delivering agent are at least partly added as one compound by using an urea adduct.

In a preferred embodiment the reactants are piperazine (PIP), and/or a mono or di aminoethyl-substituted piperazine (AEP or DAEP) as the amine-functional compound and monoethanolamine (MEA) and/or aminoethylethanolamine (AEEA) as the ethanolamine-functional compound wherein optionally one or more of these compounds may be present as a carbamate or urea derivative.

In a more preferred embodiment the ethanolamine-functional compound is MEA, CMEA or a mixture thereof and the amine-functional compound is piperazine (PIP), or a combination of EDA, EU and PIP.

Even more preferred the ratio of, the ratio MEA+CMEA to PIP, is higher than 2, yet more preferred higher than 3.

In an embodiment of the process of the invention a next step is performed to convert possibly obtained cyclic ethylene urea into its corresponding ethylene amine, though in many embodiments this step is not necessary as the product will not be a cyclic ethylene urea which cannot form on a cyclic secondary amine function.

The product mixture can be further processed or fractionated into several products that each independently are either pure compounds or mixture of compounds, some of which may be recycled.

The process of the present invention is done in a liquid which is a polar liquid, such as an alcohol or water. Doing the process of the present invention in the presence of water as a liquid or without any additional liquid is preferred.

The reactor employed can be any suitable reactor including continuously stirred tank reactor, pipeline reactor, tubular or multi-tubular reactor. The reactor may be adiabatic or equipped with external or internal heating devices. Feed may be single point or split into multiple points. It can consist of multiple stages with inter-stage heat exchange.

The process is preferably performed at a temperature of at least 100° C. The temperature should preferably be lower than 400° C. More preferably the temperature is between 120 and 320° C. Even more preferably the temperature is between 150 and 280° C. Most preferably the temperature is between 190 and 230° C.

In embodiments where the ethanolamine-functional compound is monoethanolamine the temperature is at least 100° C. The temperature should preferably be lower than 300° C. More preferably the temperature is between 120 and 280° C. Even more preferably the temperature is between 140 and 220° C. Most preferably the temperature is between 160 and 200° C.

The reaction time during the process is in an embodiment between 5 minutes and 10 hours, preferably between 0.5 and 6 hours, more preferably between 1 and 4 hours.

The process can be carried out in one or multiple batch reactors, possibly in fed-batch operation, and/or in a continuously operating system in one reactor or in a cascade of continuous flow reactors, optionally with multiple feeding points. The reaction and separation can be performed in separate steps or at least partially simultaneously. The reaction and separation can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

The person skilled in the art is capable of selecting the proper reactor and separation unit scheme by determining the overall yield, energy consumption and waste production.

Examples

Comparative Example A (Based on U.S. Pat. No. 5,262,534/Example 1)

25.48 g (1.18 mole) PIP and 21.78 g (1 mole) CMEA were charged to a 300 mL autoclave equipped with stirring and internal temperature monitoring. The reaction was then carried out for 2 h at 200° C. The resulting reaction mixture was analyzed using a GC-FID (gas chromatography using a flame ionization detector). The GC results are reported as area-%.

Examples 1-9 (Influence of Water on Product Yields for the Reaction PIP+CMEA after 30 min)

PIP and CMEA—with a similar PIP to CMEA molar ratio as in the comparative Example A of 1.18 to 1—together with varying amounts of water—0.25 to 24 molar equivalent of water relative to the amount of PIP—were charged to a 300 mL autoclave equipped with stirring and internal temperature monitoring. The reaction was then carried out for 30 min at 200° C. The resulting reaction mixture was analyzed using GC-FID. The GC results are reported as area-% in below Table 1.

Examples 1-9 clearly show that the addition of water of more than 0.2 mol-equiv. increases the conversion of PIP to AEP and DAEP compared to the reaction without water (Example A) without increasing the amount of other products formed.

Examples 10-15 (Influence of Water and Reaction Time on Product Yields for the Reaction PIP+CMEA at 200° C.)

The same experimental setup as described for Examples 1-9 was used except that the reaction time at 200° C. was varied from 30 to 150 min. Reactions were performed without added water or with 0.5 molar equivalents of water relative to the molar amount of PIP. The resulting reaction mixture was analyzed using GC-FID. The GC results are reported as area-% in below Table 2.

TABLE 2 the reaction of PIP and MEA at different reaction times with and without water

| | Example | | | | | | | |
|---|---|---|---|---|---|---|---|---|
| | A | 10 | 11 | 12 | 1 | 13 | 14 | 15 |
| | | without added H$_2$O | | | with 0.5 mol.-equiv H2O relative to n(PIP) | | | |
| reaction time in min | 30 | 60 | 120 | 150 | 30 | 60 | 120 | 150 |
| MEA | 7 | 6 | 5 | 4 | 7 | 6 | 5 | 4 |
| PIP | 52 | 43 | 46 | 39 | 49 | 41 | 36 | 35 |
| AEP | 26 | 36 | 37 | 43 | 32 | 39 | 42 | 45 |
| CMEA | 9 | 5 | 2 | 3 | 6 | 4 | 1 | 2 |
| DAEP | 2 | 4 | 6 | 6 | 3 | 6 | 9 | 8 |
| PEEDA | n.d. | n.d. | n.d. | n.d. | n.d. | n.d. | n.d. | n.d. |
| UAEEA | 1 | 1 | 1 | 1 | 1 | 1 | 1 | 1 |
| UPEEDA | 2 | 2 | 3 | 4 | 2 | 3 | 4 | 4 |
| UPEDETA | n.d. | n.d. | 1 | n.d. | n.d. | n.d. | 1 | 1 |

GC results in area-%
n.d. = below detection limits

It was shown that the addition of 0.5 moles of water per mole of PIP lead to higher AEP and DAEP yield compared to the reaction without water without increasing the amount of other products formed.

TABLE 1 reaction of PIP and MEA at several water amounts

| | Example | | | | | | | | | |
|---|---|---|---|---|---|---|---|---|---|---|
| | A | 1 | 2 | 3 | 4 | 5 | 6 | 7 | 8 | 9 |
| H$_2$O in molar equiv. relative to n(PIP) | 0 | 0.25 | 0.5 | 1 | 2.2 | 4.8 | 7.2 | 9.5 | 14.4 | 24 |
| MEA | 7 | 7 | 7 | 7 | 6 | 6 | 6 | 5 | 6 | 6 |
| PIP | 52 | 51 | 49 | 42 | 40 | 34 | 35 | 38 | 32 | 31 |
| AEP | 26 | 27 | 32 | 38 | 40 | 42 | 42 | 41 | 43 | 42 |
| CMEA | 9 | 10 | 6 | 5 | 3 | 2 | 1 | n.d. | 1 | n.d. |
| DAEP | 2 | 2 | 3 | 4 | 6 | 10 | 11 | 10 | 12 | 13 |
| PEEDA | n.d. | n.d. | n.d. | n.d. | n.d. | 1 | 1 | 1 | 1 | 1 |
| UAEEA | 1 | 1 | 1 | 1 | 1 | 1 | 1 | 1 | 1 | 1 |
| UPEEDA | 2 | 2 | 2 | 2 | 3 | 3 | 3 | 2 | 3 | 3 |
| UPEDETA | n.d. | n.d. | n.d. | n.d. | n.d. | 1 | 1 | 1 | 1 | 1 |

GC results in area-%
n.d. = below detection limits

Examples 16-21 (Influence of Water and Reaction Temperature on Product Yields for the Reaction PIP+CMEA after 2 h Reaction Time)

The same experimental setup as described for Examples 1-9 was used except that the reaction temperature was varied from 120 to 200° C. Reactions were performed without added water or with 4.8 molar equivalent of water relative to the amount of PIP. The reaction time was kept constant at 2 h. The resulting reaction mixture was analyzed using GC-FID. The GC results are reported as area-% in below Table 3.

TABLE 3 the reaction of PIP and MEA at different temperatures with and without water

| | Example | | | | | | | |
|---|---|---|---|---|---|---|---|---|
| | 16 | 17 | 18 | A | 19 | 20 | 21 | 5 |
| | without added H$_2$O | | | | 4.8 molar equiv. H$_2$O relative to n(PIP) | | | |
| temperature in ° C. | 120 | 140 | 160 | 200 | 120 | 140 | 160 | 200 |
| MEA | n.d. | 1 | 6 | 5 | n.d. | 4 | 6 | 6 |
| PIP | 66 | 67 | 59 | 46 | 57 | 50 | 44 | 34 |
| AEP | 5 | 7 | 16 | 37 | 16 | 28 | 37 | 42 |
| CMEA | 24 | 21 | 12 | 2 | 21 | 12 | 2 | 2 |
| DAEP | 1 | n.d. | 1 | 6 | 2 | 3 | 6 | 10 |
| PEEDA | n.d. | n.d. | n.d. | n.d. | n.d. | 1 | 1 | 1 |
| UAEEA | n.d. | n.d. | n.d. | 1 | n.d. | n.d. | n.d. | 1 |
| UPEEDA | n.d. | n.d. | 2 | 3 | n.d. | 1 | 2 | 3 |
| UPEDETA | n.d. | n.d. | 1 | 1 | n.d. | n.d. | 1 | 1 |

GC results in area-%
n.d. = below detection limits

In agreement with Examples 10-15 the addition of water leads to an increase in AEP and DAEP yield at the same reaction temperature which also means that—compared to the reaction without water—similar AEP and DAEP yields can be obtained at lower reaction temperatures without increasing the amount of other products formed.

Examples 22-25 (Influence of Water on Product Yields for the Reaction AEP+CMEA)

The same experimental setup as described for Examples 1-9 was used except that 1 mole AEP and 1 mole CMEA were reacted at 200° C. for 1 h without added water or with 0.5, 1, or 2 molar equivalent of water relative to the amount of AEP. The resulting reaction mixture was analyzed using GC-FID. The GC results are reported as area-% in below Table 4.

TABLE 4 reaction of AEP and MEA with different amounts of water

| Example | 22 | 23 | 24 | 25 |
|---|---|---|---|---|
| H$_2$O in molar equiv. relative to n(PIP) | 0 | 0.5 | 1 | 2 |
| MEA | 12 | 12 | 11 | 10 |
| AEP | 58 | 58 | 56 | 52 |
| CMEA | 5 | 4 | 3 | 2 |
| DAEP | 13 | 15 | 18 | 21 |
| PEEDA | n.d. | n.d. | n.d. | n.d. |
| UAEEA | 2 | 2 | 2 | 2 |

TABLE 4-continued reaction of AEP and MEA with different amounts of water

| Example | 22 | 23 | 24 | 25 |
|---|---|---|---|---|
| UPEEDA | 6 | 6 | 6 | 7 |
| UTEPA | 2 | 2 | 2 | 5 |

GC results in area-%
n.d. = below detection limits

The results show that the positive effect on the product yield of adding water is also observed when AEP is used as starting material.

Examples 26-27 (Influence of Water for Reaction PIP+UAEEA)

The same experimental setup as described for Examples 1-9 was used except 1 mole PIP was reacted with 1 mole UAEEA at 200° C. for 30 min without added water or with 2.5 molar equivalent of water relative to the amount of PIP. The resulting reaction mixture was analyzed using GC-FID. The GC results are reported as area-% in below Table 5.

TABLE 5 the reaction of PIP and AEEA with and without water

| Example | 26 | 27 |
|---|---|---|
| H$_2$O in molar equiv. relative to n(PIP) | 0 | 2.5 |
| AEEA | 4 | 12 |
| PIP | 34 | 27 |
| UAEEA | 48 | 26 |
| PEEDA | 1 | 8 |
| UPEEDA | 12 | 18 |
| highers | n.d. | 1 |

GC results in area-%
n.d. = below detection limits

Adding water to PIP and UAEEA increases the conversion of PIP and results in higher yields of PEEDA and UPEEDA.

The invention claimed is:

1. A process for preparing a piperazine unit-containing ethyleneamine of the formula:

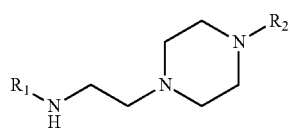

wherein R$_1$ and R$_2$ are independently selected form H and —(C$_2$H$_4$NH)$_p$H,
wherein p is at least 1 and optionally i) one or more units —NH—C$_2$H$_4$—NH— are present as a piperazine unit:

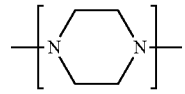

or a cyclic ethylene urea unit:

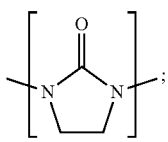

or ii) a carbonyl moiety is present between two —NH—C$_2$H$_4$—NH— units;

said process comprising reacting an ethanolamine-functional compound and an amine-functional compound in the presence of a carbon oxide delivering agent, in a liquid that comprises water, and at a temperature of at least 160° C. for a reaction time of between 5 minutes and 10 hours;

wherein:

the ethanolamine functional compound contains a hydroxyl group linked via an ethylene group to an amine group, or a linear or cyclic carbamate derivative thereof, or is UAEEA (the cyclic urea of aminoethylethanolamine)

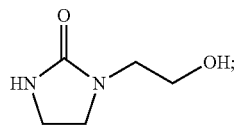

the amine functional compound contains no alcohol groups, and contains one or more amine groups, or the amine functional compound is the cyclic urea of ethylenediamine (EU)

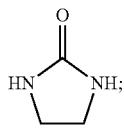

the carbon oxide delivering agent is carbon dioxide or an organic compound selected from urea, linear and cyclic alkylene ureas, mono- or di-substituted alkylene ureas, alkyl and dialkyl ureas, linear and cyclic carbamates, organic carbonates, and derivatives or precursors thereof selected from carbonate salts, bicarbonate salts and carbamic acids and their salts;

wherein at least one of the amine-functional compound or the ethanolamine-functional compound contains a piperazine unit; and wherein the molar ratio of water to the amine-functional compound is greater than 0.2:1 and less than 4.8:1.

2. The process of claim 1, wherein the ethanolamine-functional compound is of the formula HO—(C$_2$H$_4$—NH—)$_q$H wherein q is at least 1; and the amine functional compound is of the formula NH$_2$—(C$_2$H$_4$—NH—)$_r$H wherein r is at least 1 and one or more —NH—C$_2$H$_4$—NH— units are present as a piperazine unit; wherein optionally one or more —NH—C$_2$H$_4$—NH— units may be present as a cyclic ethylene urea unit; and wherein optionally one or more —O—C$_2$H$_4$—NH— units are present as a cyclic ethylene carbamate unit.

3. The process of claim 1, wherein the amine-functional compound is selected from the group consisting of (a) piperazine (PIP), (b) aminoethylpiperazine (AEP), (c) diaminoethylpiperazine (DAEP), (d) piperazinoethyl ethylenediamine (PEEDA), and a linear urea of any one of (a)-(d).

4. The process of claim 1, wherein the ethanolamine-functional compound is monoethanolamine (MEA) or a cyclic or linear carbamate thereof; or aminoethylethanolamine (AEEA) or a cyclic or linear carbamate or urea derivative thereof.

5. The process of claim 1, wherein the liquid comprises at least 75 wt-% of water based on a total weight of the liquid.

6. The process of claim 1, wherein the molar ratio of ethanolamine-functional compound to amine-functional compound is at least 0.7:1.

7. The process of claim 1, wherein the molar ratio of carbon oxide delivering agent to amine functional compound is at least 0.2:1.

8. The process of claim 1, wherein the molar ratio of ethanolamine-functional compound to amine-functional compound is between 0.8 and 5:1 and the molar ratio of carbon oxide delivering agent to amine functional compound is between 0.5:1 and 20:1.

9. The process of claim 1, wherein the molar ratio of ethanolamine-functional compound to amine-functional compound is between 0.7:1 and 2:1 and the molar ratio of carbon oxide delivering agent to amine-functional compound is between 0.7:1 and 3:1.

10. The process of claim 1, wherein the ethanolamine-functional compound and the carbon oxide delivering agent are at least partly added as one compound by using a carbamate adduct.

11. The process of claim 1, wherein the ethanolamine-functional compound is monoethanolamine (MEA), the cyclic carbamate of MEA (CMEA) or a mixture thereof and the amine-functional compound is PIP or a mixture of PIP, ethylenediamine (EDA) and the cyclic urea of EDA (EU), and wherein the molar ratio of MEA+CMEA to EDA+EU+PIP is higher than 2.

12. A process for producing an ethylene amine, said process comprising:
(a) preparing an ethylene amine compound containing a cyclic ethylene urea moiety according to the process of claim 1; and
(b) converting said ethylene amine compound containing a cyclic ethylene urea moiety into its corresponding ethylene amine.

13. The process of claim 1, wherein the molar ratio of water to the amine-functional compound is greater than 0.5:1.

14. The process of claim 1, wherein the molar ratio of water to the amine-functional compound is greater than 1:1.

15. The process of claim 11, wherein the molar ratio of MEA+CMEA to EDA+EU+PIP is higher than 3.

* * * * *